United States Patent
Liu et al.

(10) Patent No.: US 12,312,612 B2
(45) Date of Patent: May 27, 2025

(54) ACID PHOSPHATASE MUTANTS AND METHODS OF USING THE SAME

(71) Applicant: Jiangnan University, Wuxi (CN)

(72) Inventors: Liming Liu, Wuxi (CN); Xin Xu, Wuxi (CN); Wei Song, Wuxi (CN); Xiulai Chen, Wuxi (CN); Jia Liu, Wuxi (CN); Cong Gao, Wuxi (CN); Jing Wu, Wuxi (CN); Liang Guo, Wuxi (CN)

(73) Assignee: Jiangnan University, Wuxi (CN)

( * ) Notice: Subject to any disclaimer, the term of this patent is extended or adjusted under 35 U.S.C. 154(b) by 557 days.

(21) Appl. No.: 17/694,779

(22) Filed: Mar. 15, 2022

(65) Prior Publication Data
US 2022/0204953 A1 Jun. 30, 2022

Related U.S. Application Data

(63) Continuation of application No. PCT/CN2021/096674, filed on May 28, 2021.

(30) Foreign Application Priority Data

Apr. 12, 2021 (CN) .......................... 202110388771.2

(51) Int. Cl.
C12N 9/16 (2006.01)
C12N 15/70 (2006.01)
C12P 17/04 (2006.01)

(52) U.S. Cl.
CPC .............. *C12N 9/16* (2013.01); *C12N 15/70* (2013.01); *C12P 17/04* (2013.01); *C12Y 301/03002* (2013.01)

(58) Field of Classification Search
None
See application file for complete search history.

(56) References Cited

U.S. PATENT DOCUMENTS 10,308,919 B2 * 6/2019 Liu ..................... C12N 9/16
2022/0204953 A1 * 6/2022 Liu ..................... C12N 9/16

FOREIGN PATENT DOCUMENTS

CN 106282081 A * 1/2017 ............. C12N 15/70

OTHER PUBLICATIONS

KAI Zheng et. al. "Enzymatic production of ascorbic acid-2-phosphate by recombinant acid phosphatase" J Agric Food Chem. May 24, 2017, V20, No. 65.
Krishnendu Pramanik et. al. "An in silico structural, functional and phylogenetic analysis with three dimensional protein modeling of alkaline phosphatase enzyme of Pseudomonas aeruginosa" J Genet Eng Biotechnol. Jun. 12, 2017 V2, No. 15.
Carlos E. Domenech et. al. "Pseudomonas aeruginosa acid phosphatase activation by divalent cations and inhibition by alumninium io" FEBS Letters Mar. 2, 1992, V1, N 299.
Sequence 2 from patent US 100308919 GenBank: QFN31972.1, Oct. 10, 2019.

* cited by examiner

*Primary Examiner* — Hope A Robinson
(74) *Attorney, Agent, or Firm* — IPRO, PLLC; Na Xu

(57) ABSTRACT

Disclosed is an acid phosphatase mutant obtained from *Pseudomonas aeruginosa* having the amino acid sequence of SEQ ID NO:3 and method of using the mutant in the technical field of biological engineering. The disclosure provides a mutant of acid phosphatase PaAPase$_{Mu3}$. By expressing the mutant of acid phosphatase PaAPase$_{Mu3}$ in *Escherichia coli* and using a whole-cell conversion method, L-ascorbic acid is transformed into L-ascorbate-2-phosphate. Moreover, the problems of a high substrate cost, environmental pollution and the like are greatly reduced, laying a foundation for the industrial green production of L-ascorbate-2-phosphate.

1 Claim, 3 Drawing Sheets
Specification includes a Sequence Listing.

ACID PHOSPHATASE MUTANTS AND METHODS OF USING THE SAME

TECHNICAL FIELD

The disclosure relates to a mutant of acid phosphatase and an application thereof, belonging to the technical field of biological engineering.

BACKGROUND

L-ascorbate-2-phosphate is a derivative of L-ascorbic acid, with a chemical formula $C_6H_6O_9P$. The carbon skeleton of L-ascorbic acid is bridged with a phosphate group at site 2.

At present, a main production method of L-ascorbate-2-phosphate is chemical synthesis which primarily employs a group protection method. However, despite a high yield, such method requires a large energy consumption, and causes a toxic effect on the environment, thereby not meeting the requirements for green production, safe production and sustainable development. Biological preparation of L-ascorbate-2-phosphate has the characteristics of stable product quality, safety, mild technological conditions, high efficiency, environmental friendliness and the like, and can relieve pressures on the environment and resources, thereby prompting an urgent need for an effective and efficient biological preparation method of L-ascorbate-2-phosphate.

At present, microbial production of L-ascorbate-2-phosphate involves a key enzyme, acid phosphatase, which has a broad substrate spectrum and can catalyze L-ascorbic acid for phosphorylation of site C2 thereof, to form L-ascorbate-2-phosphate. The microbial preparation of L-ascorbate-2-phosphate primarily adopts an enzyme conversion method. At present, the enzyme conversion method has value in industrial application due to its advantages such as environmental friendliness, mild reaction conditions and easy operation.

SUMMARY

Disclosed is a mutant of acid phosphatase, having an amino acid sequence shown by SEQ ID NO: 3.

Disclosed is a mutant of acid phosphatase, taking acid phosphatase from *Pseudomonas aeruginosa* as a parent enzyme, wherein an amino acid sequence of the acid phosphatase is shown by SEQ ID NO: 1, and at least one of sites 57, 58, 94 and 135 of the parent enzyme is mutated.

In an embodiment, the mutant meets any one of situations (a)-(f):
  (a) the site 58 is mutated into F, wherein an amino acid sequence of the mutant is shown by SEQ ID NO: 17;
  (b) the site 94 is mutated into F, wherein an amino acid sequence of the mutant is shown by SEQ ID NO: 18;
  (c) the site 135 is mutated into R, wherein an amino acid sequence of the mutant is shown by SEQ ID NO: 19;
  (d) the site 94 is mutated into F, and the site 135 is mutated into R, wherein an amino acid sequence of the mutant is shown by SEQ ID NO: 20;
  (e) the site 58 is mutated into P, and the site 135 is mutated into R, wherein an amino acid sequence of the mutant is shown by SEQ ID NO: 21; and
  (f) the site 57 is mutated into H, the site 58 is mutated into P, and the site 135 is mutated into R, wherein an amino acid sequence of the mutant is shown by SEQ ID NO: 22.

Disclosed is a gene coding the mutant.

Disclosed is a recombinant plasmid carrying the gene.

Disclosed is a microbial cell expressing the mutant, or carrying the recombinant plasmid.

In an embodiment, the microbial cell takes *Escherichia coli* as a host cell.

Disclosed is a method for synthesizing L-ascorbate-2-phosphate, transforming L-ascorbic acid as a substrate by using the microbial cell, to produce L-ascorbate-2-phosphate.

In an embodiment, the microbial cell according to claim 5 is added to a reaction system containing L-ascorbic acid and sodium pyrophosphate, the reaction system having a pH of 3.8-4.3.

In an embodiment, the pH of the reaction system is 4.0-4.2.

In an embodiment, the reaction at 25-37° C. lasts for not less than 8 h.

In an embodiment, the reaction at 25-30° C. lasts for not less than 10 h.

In an embodiment, a concentration of the microbial cells in the reaction system is 20-40 g/L, a concentration of the L-ascorbic acid is 70-100 g/L, and a concentration of the sodium pyrophosphate is 180-240 g/L.

In an embodiment, the concentration of the microbial cells in the reaction system is 30 g/L, the concentration of the L-ascorbic acid is 88 g/L, and the concentration of the sodium pyrophosphate is 223 g/L.

In an embodiment, the concentration of the microbial cells in the reaction system is 25-35 g/L, the concentration of the L-ascorbic acid is 70-90 g/L, and the concentration of the sodium pyrophosphate is 200-240 g/L.

The disclosure provides an application of the mutant or the microbial cells in preparing L-ascorbate-2-phosphate, products containing L-ascorbate-2-phosphate, and derivatives of L-ascorbate-2-phosphate.

The disclosure provides an application of the microbial cells in preparing L-ascorbate-2-phosphate, products containing L-ascorbate-2-phosphate, and derivatives of L-ascorbate-2-phosphate.

Beneficial effects of the disclosure: The disclosure provides a mutant of acid phosphatase PaAPase$_{Mu3}$ for catalysis to produce L-ascorbate-2-phosphate. The mutant of acid phosphatase not only greatly improves the catalytic efficiency of the mutant of acid phosphatase, but also effectively reduces the production cost due to a quite low hydrolysis capability against the product. When the mutant of acid phosphatase disclosed by the disclosure takes L-ascorbic acid as a substrate, a yield of L-ascorbate-2-phosphate can reach 90.1 g/L, and a molar yield can reach 75.1%, thereby accelerating the industrialization of producing L-ascorbate-2-phosphate by an enzyme conversion method.

Figure 1:
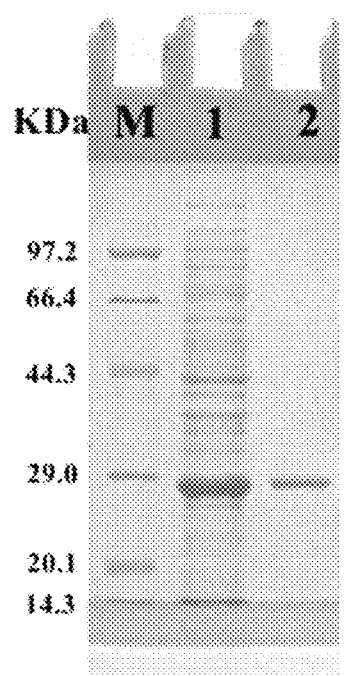
FIG. 1 is an SDS-PAGE diagram of the mutant of acid phosphatase PaAPase$_{Mu3}$.

DETAILED DESCRIPTION (1) Liquid Chromatographic Analysis:

A liquid chromatograph Waters ACQUITY UPLC™ is adopted for sample analysis.

Composition of a mobile phase: 1 L of 0.1 mol·L$^{-1}$ KH$_2$PO$_4$ solution is prepared with ultrapure water, then 500 mL of acetonitrile is added, and the two were mixed together. The pH of the mixed solution is adjusted with phosphoric acid to 3.0. The mobile phase is subjected to vacuum filtration by a 0.22 μm organic filter membrane, and then 20 min of ultrasonic degassing is performed.

Sample introduction procedure: One sample is introduced every 8 minutes, where the sampling amount of each sample is 12 μL.

Elution procedure: The flow rate of the mobile phase is constant at 1 mL·min$^{-1}$.

Chromatographic column: APS-2 HYPERSIL column (150 mm×4.6 mm, 5 μm) at 35° C.

Detector: The ultraviolet absorption wavelength is 254 nm.

(2) Protein purification:

An ultrasonic cell disruptor is employed to perform an ultrasonic treatment on cells containing a target plasmid, at a power of 36% and at an interval of 3 s for every 2 s of work, till complete disruption, to obtain a whole-cell disruption liquid. The cell disruption liquid is centrifuged in a refrigerated centrifuge at a temperature of 4° C. and at a speed of 12,000 rpm for 30 min. After the centrifugation, the supernatant is filtered with a 0.22 μm water-based filter membrane, and then the filtrate is collected. The filtrate is purified with a purifier of an AKTAxpress system, using a 5 mL HisTrap HP purifying column as a purifying column. In elution, a buffer solution (20 mM Tris-HCl, 150 mM NaCl) containing 1 M imidazole is used for elution at a flow rate of 2-3 mL·min$^{-1}$. Then, the purified components are verified through 10% (w/v) sodium dodecyl sulfate-polyacrylamide gel electrophoresis (SDS-PAGE). The purest component is desalted using a PD-10 desalting column and a low-salt buffer solution (10 mM Tris-HCl, 0.1 M NaCl; pH 6.0). The purified and desalted proteins are collected.

(3) Sequences of primers used in examples:

TABLE 1

Primers used during mutation

| Name | Primer (5'-3') | |
|---|---|---|
| D56-F | GCGCATNNKCAGTGGGAAGAT | SEQ ID NO: 3 |
| D56-R | CCACTGMNNATGCGCGCAC | SEQ ID NO: 4 |
| W58-F | GATCAGNNKGAAGATAACGTG | SEQ ID NO: 5 |
| W58-R | ATCTTCMNNCTGATCATGCGC | SEQ ID NO: 6 |
| V94-F | CAAGAAAACCTGNNKGAAGTG | SEQ ID NO: 7 |
| V94-R | CATCAGCACTTCMNNCAGGTT | SEQ ID NO: 8 |
| D135-F | GGCCATACCATGNNKAGCTAT | SEQ ID NO: 9 |
| D135-R | TTTAAAATAGCTMNNCATGGT | SEQ ID NO: 10 |
| W58P/D135R/Q57L-F | CGCGCGCATGATAAACCAGAA | SEQ ID NO: 11 |
| W58P/D135R/Q57L-R | GTTATCTTCTGGTTTATCATG | SEQ ID NO: 12 |
| W58P/D135R/Q57R-F | CGCGCGCATGATAGGCCAGAA | SEQ ID NO: 13 |
| W58P/D135R/Q57R-R | GTTATCTTCTGGCCTATCATG | SEQ ID NO: 14 |
| W58P/D135R/Q57H-F | CGCGCGCATGATCACCCAGAA | SEQ ID NO: 15 |
| W58P/D135R/Q57H-R | GTTATCTTCTGGGTGATCATG | SEQ ID NO: 16 |

Example 1: Construction and Screening of Mutants of a PaAPase Enzyme

Taking a PaAPase enzyme having an amino acid sequence shown by SEQ ID NO: 1 as a parent (the nucleotide sequence of a coding gene thereof was shown by SEQ ID NO: 2), saturation mutation (the primers used were shown in Table 1) was performed at sites 56, 58, 135 and 94 thereof, and beneficial mutants were screened out.

A fragment obtained by PCR was connected to pET-28a (+) carriers (Bam H I and Hind III enzymes), and whole-plasmid PCR was performed using corresponding primers in Table 1, to obtain recombinant plasmids containing mutants. The recombinant plasmids were transferred into *Escherichia coli*, to construct recombinant bacteria. The recombinant bacteria were spread on a LB plate having kanamycin resistance, and cultured at 37° C. to grow monoclones.

A sterile 96-well deep-well plate (first-level plate) was opened in a super clean bench. 400 µL of a LB medium (containing 0.1 g·L$^{-1}$ kanamycin) was added into each well with a multichannel pipette. *Escherichia coli* transformants for saturation mutation on the LB plate were picked with a toothpick and inoculated into the 96-well deep-well plate, where original strains were added into the plate wells in column 12 as controls. Overnight culture was performed in a high-throughput shaker at 37° C. and 600 rpm. 50 µL of a seed solution in the first-level plate was fetched with a multichannel pipette and inoculated into a 96-well deep-well plate (second-level plate) containing 800 µL of a lactose auto-induction medium (containing 0.1 g·L$^{-1}$ kanamycin) in each well, and cultured at 37° C. and 600 rpm for 3-4 h (with $OD_{600}$ around 1). The temperature of the high-throughput shaker was adjusted to 25° C., and induction was performed for 12 h. Then, the resulting product was centrifuged at 3,000×g for 5 min. The supernatant in the 96-well deep-well plate (second-level plate) was discarded while the cells were collected and stored at −80° C. for later use. The 96-well deep-well plate containing mutant cells frozen at −80° C. was taken out, and placed at room temperature for 30 min for defrosting. Then, 200 µL of a substrate solution (4 g·L$^{-1}$ L-ascorbic acid, 30 g·L$^{-1}$ pyrophosphoric acid, pH 4.0) was added into each well with a multichannel pipette. Through repeated blowing and suction with the multichannel pipette, the cells were suspended in the substrate solution. Then the cell suspension was maintained at a temperature of 25° C. for 16 h. The cell suspension was centrifuged at 3,000×g for 20 min for separation and precipitation. The supernatant in the deep-well plate was taken out, diluted by 5 times, and measured with HPLC. A molar conversion rate was calculated.

According to the HPLC results and by sequencing, 3 beneficial mutants, W58F, V94F and D135R, were screened out, with molar conversion rates of 37.6%, 41.3% and 45.3% respectively.

Based on the 3 beneficial mutants, W58F, V94F and D135R were subjected to combinatorial mutations according to the foregoing steps (mutations using corresponding primers based on single mutants, to construct double mutants), and conversion efficiency was determined according to step 2.

The results showed that the conversion rates of the combinatorial mutants, W58F/D135R, W58F/V94F and V94F/D135R, were 19.7%, 17.9% and 40.9% respectively, all lower than that of D135R. Therefore, PaAPase$_{Mu1}$ (D135R) was selected as a template to carry out site-saturation mutation on Trp58 and Val94.

The results showed that in the double mutants, the conversion rate of PaAPase$_{Mu2}$ (W58P/D135R) was increased by 1.56 times. Taking PaAPase$_{Mu2}$ (W58P/D135R) as a template, Gln57 was mutated into positive amino acid (Lys, Arg and His), where the conversion rate of PaAPase$_{Mu3}$ (Q57H/W58P/D135R) was increased by 1.9 times from that of a wild type.

TABLE 2

Conversion effects of mutants

| Mutant | Conversion rate (%) | Yield |
|---|---|---|
| WT | 25.9 | 31.08 |
| W58F | 37.6 | 45.12 |
| V94F | 41.3 | 51.96 |
| D135R | 45.3 | 54.36 |
| W58F/D135R | 19.7 | 23.64 |
| V94F/D135R | 40.9 | 49.08 |
| W58F/V94F | 17.9 | 21.48 |
| W58P/D135R | 62.1 | 79.32 |
| Q57H/W58P/D135R | 75.1 | 90.10 |

Example 2: Enzymatic Properties of Mutants

The obtained recombinant bacteria containing PaAPase$_{Mu3}$ (Q57H/W58P/D135R) were introduced into a LB medium, and cultured for 12 h to obtain an activated liquid. The activated liquid was inoculated into a fresh TB medium, and cultured for 2 h. Then, IPTG with a final concentration of 0.2 mM was added. The mixture was cultured at 25° C. for 14 h, to induce expression of a recombinant target protein. The enzyme liquid was collected and subjected to ultrasonic disruption, and then albumin glue verification was performed (FIG. 1). In FIG. 1, M is marker, 1 is a band of a crude enzyme liquid, and 2 is a band of the purified target protein (29 KDa). The other mutants were expressed and purified with the same method.

(1) Determination of Specific Enzyme Activity

The activities of PaAPase and mutants thereof were determined with high-performance liquid chromatography. 500 µL of a substrate solution (500 mM L-ascorbic acid and 500 mM sodium pyrophosphate) (pH 5.0) and 5 µL of the enzyme liquid react at 30° C. for 30 min, and 95 µL of 42% phosphoric acid was added to terminate the reaction, where an activity unit was defined as the amount of enzyme required for producing 1 µmol of L-ascorbate-2-phosphate within 1 min (Table 3).

(2) Determination of Kinetic Parameters

The kinetic parameters, including $V_{max}$, $K_m$ and $k_{cat}$, were calculated by measuring the generation rates of initial products of L-ascorbic acid and L-ascorbate-2-phosphate (1-1, 000 mM) at different concentrations at 30° C. and under other conditions consistent with those of the determination of specific enzyme activity. The determination of all activities was repeated three times, with the results shown in Table 3.

TABLE 3

Specific enzyme activities and kinetic parameters of mutants

| Enzyme | Specific Enzyme Activity (U mg$^{-1}$) | $K_m$ (mM) | $k_{cat}$ (s$^{-1}$) | $k_{cat}/K_m$ (min$^{-1}$ · mM$^{-1}$) |
|---|---|---|---|---|
| WT | 14.8 | 289 | 16.3 | 3.38 |
| Mu1/(D135R) | 28.1 | 245 | 18.7 | 4.58 |
| Mu2 (W58P/D135R) | 32.3 | 223 | 19.2 | 5.17 |
| Mu3 (Q57H/W58P/D135R) | 39.7 | 211 | 20.1 | 5.72 |

(3) Impact of pH on PaAPase$_{Mu3}$ Activity

Figure 2:
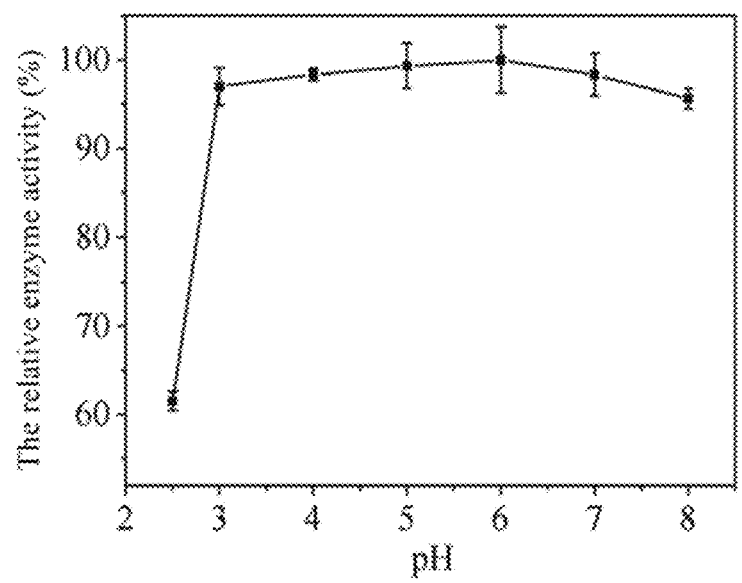
FIG. 2 is a diagram illustrating the enzyme activities of the mutant of acid phosphatase at different pHs.
Figure 3:
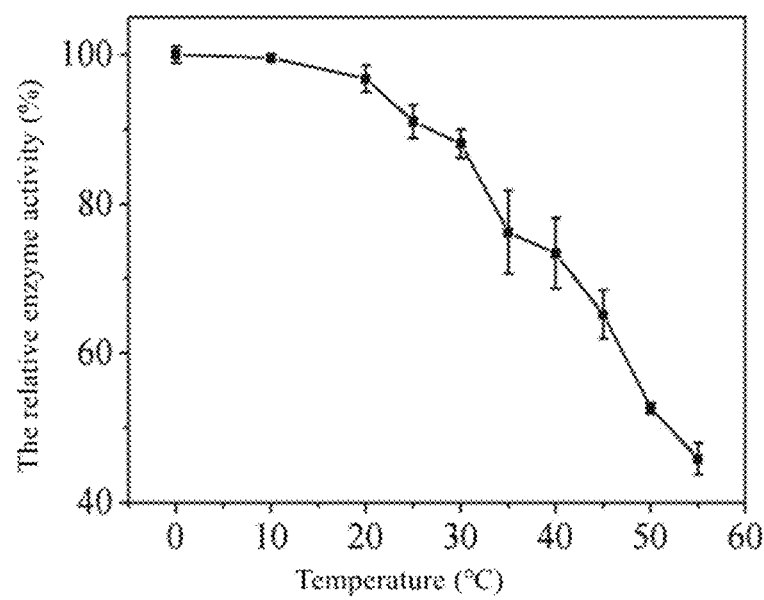
FIG. 3 is a diagram illustrating the enzyme activities of the mutant of acid phosphatase at different temperatures.

The pH stability of PaAPase was detected within a pH range from 2.5 to 8.0. From FIG. 2, the enzyme activity of PaAPase was lost a little after 12 h of storage at 4° C. and at a pH of 3.0-8.0, and the remaining enzyme activity was 90% or above. However, when the pH was below 2.5, the remaining activity of PaAPase was only 60% of the initial enzyme activity. The above-mentioned results indicate that PaAPase has excellent pH stability at a pH of 3.0-8.0, and the enzyme activity undergoes a relatively large loss in a strong acid condition.

(4) Impact of Temperature on PaAPase$_{Mu3}$ Activity

The temperature stability of PaAPase was detected at 0-55° C., with the results shown in Table 3. PaAPase was relatively stable in an environment below 20° C., and 90% or above of the initial activity of PaAPase could be maintained. When the temperature was between 20° C. and 55° C., the loss of enzyme activity was increased gradually. After standing for 1 h at 50° C., the loss of enzyme activity was close to 50%. The above-mentioned results indicate that an increasing temperature promotes catalysis of protease molecules. But as the temperature rises, a trend of protein denaturation and inactivation becomes more obvious. When the temperature exceeds 50° C., the enzyme activity starts to decrease sharply mainly because a large number of proteins are denaturalized and inactivated at the time. At 25-50° C., an increasing temperature increases the enzyme catalytic activity in a reaction system by an amount larger than the loss of activity caused by protein denaturation, thereby leading to an overall increasing trend of the enzyme activity.

Example 3: Whole-Cell Production of L-Ascorbate-2-Phosphate Using Recombinant Bacteria PaAPase$_{Mu3}$ (1) Whole-Cell Optimum Reaction pH The strains stored in a glycerin tube were spread on a LB solid medium, and cultured at a constant temperature of 37° C. to grow monoclones. The monolclones were picked and placed into a fresh LB liquid medium, and cultured at a constant temperature of 37° C. and at 200 rpm for 12 h, to obtain an activated liquid. The activated liquid was inoculated into a fresh TB medium, and cultured for 2 h. Then, IPTG with a final concentration of 0.2 mM was added, and induction culture was performed at 25° C. for 14 h. After the culture, the cells were collected.

3 g of the whole cells expressing PaAPase$_{Mu3}$ protein after the induction culture were added into each of 100 mL conical flasks respectively, and were reacted at 25° C. for 12 h in reaction systems with a pH of 3.0, 3.5, 4.0, 4.5 and 5.0 respectively, the reaction systems containing 88 g/L L-ascorbic acid, 223 g/L sodium pyrophosphate and hydrochloric acid for adjusting pH. Then, the resulting products passed through a 0.22 μm water membrane, and liquid chromatographic analysis was carried out.

Figure 4:
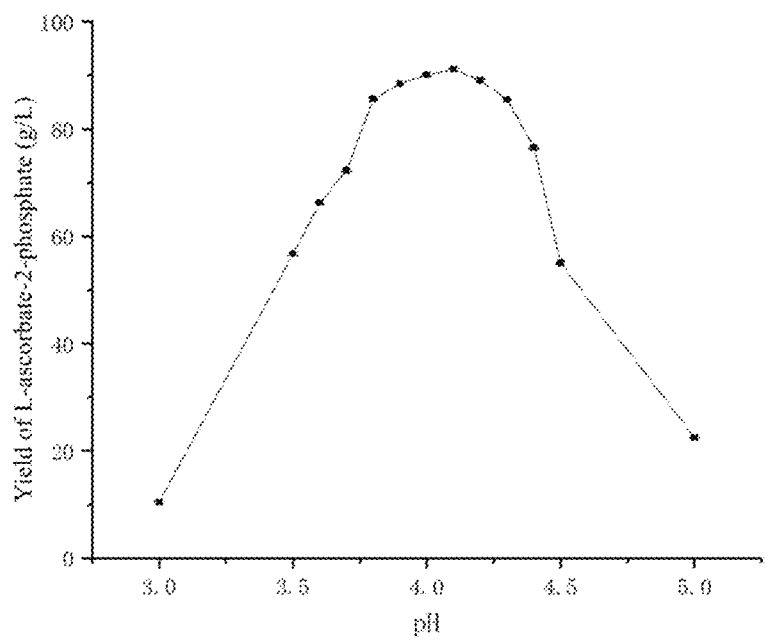
FIG. 4 is a diagram illustrating a relationship between the pH of a buffer solution of the conversion system and the yield of L-ascorbate-2-phosphate.

The yield of L-ascorbate-2-phosphate was determined with the foregoing detection method. The results are shown in Table 4 and FIG. 4 that the conversion rate of the PaAPase$_{Mu3}$ enzyme at a pH of 3.0-4.0 is increased as the pH rises. The yield of L-ascorbate-2-phosphate can reach 85 g/L or more at a pH of 3.8-4.3 and 90.1 g/L at a pH of 4.0 while the molar yield is 75.1%. The yield of L-ascorbate-2-phosphate is reduced with further increase of the pH.

TABLE 4

Yield of L-ascorbate-2-phosphate at different pHs

| pH | Yield of L-ascorbate-2-phosphate (g/L) |
|---|---|
| 3 | 10.4 |
| 3.5 | 56.7 |
| 3.6 | 66.2 |
| 3.7 | 72.3 |
| 3.8 | 85.6 |
| 3.9 | 88.5 |
| 4.0 | 90.1 |
| 4.1 | 91.1 |
| 4.2 | 89.1 |
| 4.3 | 85.5 |
| 4.4 | 76.5 |
| 4.5 | 55 |
| 5 | 22.5 |

(2) Whole-Cell Optimum Reaction Temperature

Figure 5:
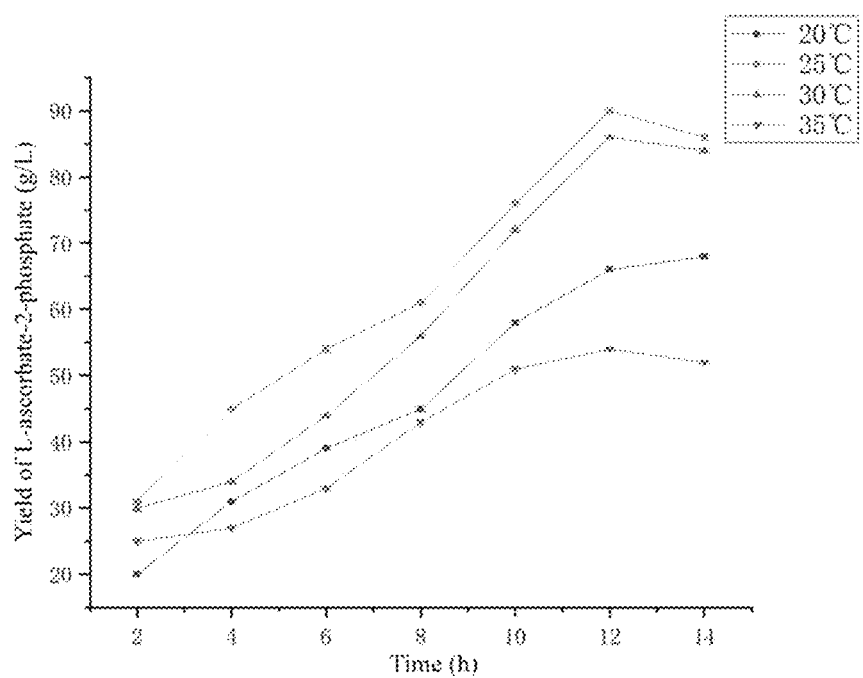
FIG. 5 is a diagram illustrating a relationship between the conversion temperature and the yield of L-ascorbate-2-phosphate.

According to the steps in (1), the yield of L-ascorbate-2-phosphate after 14 h of conversion of PaAPase$_{Mu3}$ at different temperatures (20° C., 25° C., 30° C. and 37° C.) was determined every 2 hours at a pH of 4 of the reaction system, and a molar yield was calculated. The results are shown in FIG. 5 that the PaAPase$_{Mu3}$ enzyme can lead to a relatively high yield of L-ascorbate-2-phosphate at 25-30° C. The conversion temperature of 25-30° C. is more favorable for the catalysis of a phosphorylation reaction by the PaAPase$_{Mu3}$ enzyme. At 25° C., the conversion rate is the highest, the yield of L-ascorbate-2-phosphate is 90.1 g/L, and the molar yield is 75.1%. At 30° C., the yield of L-ascorbate-2-phosphate is 84 g/L, and the molar yield is 70%.

Although the disclosure is described above using preferred examples, the disclosure is not limited thereto. Those skilled in the art can make various changes and modifications without departing from the spirit and scope of the disclosure. Therefore, the scope of the disclosure shall be subject to the definition of the claims.

What is claimed is:

1. An acid phosphatase mutant, wherein the acid phosphatase mutant is from *Pseudomonas aeruginosa (P. aeruginosa)*,
wherein the acid phosphatase mutant comprises the amino acid sequence of SEQ ID NO:1 with mutations at any one or more of sites 57, 58, 94, or 135 of SEQ ID NO: 1,
wherein the acid phosphatase mutant possesses a catalytic efficiency that is greater than the catalytic efficiency of a corresponding wild type acid phosphatase from *P. aeruginosa*, and
wherein the mutations are in any one or more of (a)-(f):
(a) the site 58 is mutated into phenylalanine;
(b) the site 94 is mutated into phenylalanine;
(c) the site 135 is mutated into arginine;
(d) the site 94 is mutated into phenylalanine, and the site 135 is mutated into arginine;
(e) the site 58 is mutated into proline, and the site 135 is mutated into arginine; or
(f) the site 57 is mutated into histidine, the site 58 is mutated into proline, and the site 135 is mutated into arginine.

* * * * *

SEQUENCE LISTING

```
<160> NUMBER OF SEQ ID NOS: 22

<210> SEQ ID NO 1
<211> LENGTH: 217
<212> TYPE: PRT
<213> ORGANISM: Pseudomonas aeruginosa
```

<400> SEQUENCE: 1

```
Glu Thr Ala Ala Ala Pro Tyr Pro Leu Ala His Pro Pro Arg Leu Ala
1               5                   10                  15

Asp Tyr Leu Pro Pro Pro Ala Ala Asp Ser Ala Ala Ala Val Ala
            20                  25                  30

Asp Leu Gly Ala Val Leu Glu Ala Gln Arg Leu Arg Thr Pro Glu Gln
        35                  40                  45

Val Arg Arg Val Arg Ala His Asp Gln Trp Glu Asp Asn Val Phe Pro
50                  55                  60

Phe Ala Gly Asp Leu Leu Gly Ala Ser Phe Asp Lys Glu Arg Leu Pro
65                  70                  75                  80

Leu Thr Arg Ser Phe Phe Asn Arg Ala Gln Glu Asn Leu Val Glu Val
                85                  90                  95

Leu Met Pro Ala Lys Lys His Phe Ala Arg Pro Arg Pro Tyr Glu Val
            100                 105                 110

Thr Pro Lys Val Lys Pro Val Leu Pro Pro Glu Gly Glu Ser Tyr
            115                 120                 125

Pro Ser Gly His Thr Met Asp Ser Tyr Phe Lys Ala Ser Leu Leu Ser
130                 135                 140

Met Leu Val Pro Glu His His Asp Ala Phe Phe Ala Arg Ala Glu Glu
145                 150                 155                 160

His Ala Gln Ser Arg Val Leu Ala Gly Val His Phe Pro Ser Asp Leu
                165                 170                 175

Glu Gly Gly Gln Thr Ala Ala Ala Leu Val Ala Ser Leu Leu Ala
            180                 185                 190

Asp Pro Ala Val Ala Asp Phe Ala Ala Val Arg Glu Glu Leu Arg
            195                 200                 205

Gly Ala Leu Gly Leu Pro Lys Leu Gln
210                 215
```

<210> SEQ ID NO 2
<211> LENGTH: 654
<212> TYPE: DNA
<213> ORGANISM: Artificial Sequence
<220> FEATURE:
<223> OTHER INFORMATION: Synthetic DNA

<400> SEQUENCE: 2

```
gaaacagcgg cggcgccgta tcctcttgcg catccgccgc gccttgctga ttatctgcca    60
ccgcccccgg cggcagatag cgcggcagcg gttgccgatt tgggcgcggt gctagaagct   120
cagcgcctac gcaccccgga acaagtgcgc cgcgtgcgcg cgcatgatca gtgggaagat   180
aacgtgtttc cgtttgcggg cgatctgctg ggcgcgagct tgataaaga acgcctgccg   240 ctgacccgca gcttttttaa ccgcgcgcaa gaaaacctgg tggaagtgct gatgccggcg   300
aaaaaacatt ttgcgcgccc gcgcccgtat gaagtgaccc cgaaagtgaa accggtgctg   360
ccgccgccgg aaggcgaaag ctatccgagc ggccatacca tggatagcta tttaaagcg   420 agcctgctta gcatgctggt gccggaacat catgatgcgt tttttgcgcg cgcggaagaa   480
catgcgcaga gccgcgtgct ggcgggcgtg catttcccta cgacctgga gggcggtcag   540 acggcggcgg cagcgctcgt tgcgagtttg ttagccgatc cggcggtggc cgcggatttc   600
gcggccgtcc gagaagagct gcgcggcgcg ctgggcctgc gaaactgca gtaa          654
```

<210> SEQ ID NO 3

```
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(8)
<223> OTHER INFORMATION: n is a, c, g, or t

<400> SEQUENCE: 3
gcgcatnnkc agtgggaaga t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(9)
<223> OTHER INFORMATION: n is a, c, g, or t

<400> SEQUENCE: 4
ccactgmnna tgcgcgcgca c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(8)
<223> OTHER INFORMATION: n is a, c, g, or t

<400> SEQUENCE: 5
gatcagnnkg aagataacgt g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(9)
<223> OTHER INFORMATION: n is a, c, g, or t

<400> SEQUENCE: 6
atcttcmnnc tgatcatgcg c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(14)
<223> OTHER INFORMATION: n is a, c, g, or t

<400> SEQUENCE: 7
caagaaaacc tgnnkgaagt g                                              21
```

-continued

```
<210> SEQ ID NO 8
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(15)
<223> OTHER INFORMATION: n is a, c, g, or t

<400> SEQUENCE: 8
catcagcact tcmnncaggt t                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(14)
<223> OTHER INFORMATION: n is a, c, g, or t

<400> SEQUENCE: 9
ggccatacca tgnnkagcta t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(15)
<223> OTHER INFORMATION: n is a, c, g, or t

<400> SEQUENCE: 10
tttaaaatag ctmnncatgg t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
cgcgcgcatg ataaaccaga a                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
gttatcttct ggtttatcat g                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA
```

<400> SEQUENCE: 13
cgcgcgcatg ataggccaga a                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
gttatcttct ggcctatcat g                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
cgcgcgcatg atcacccaga a                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
gttatcttct gggtgatcat g                                              21

<210> SEQ ID NO 17
<211> LENGTH: 217
<212> TYPE: PRT
<213> ORGANISM: Artificial Sequence
<220> FEATURE:
<223> OTHER INFORMATION: Protein translated from synthetic DNA

<400> SEQUENCE: 17

```
Glu Thr Ala Ala Ala Pro Tyr Pro Leu Ala His Pro Pro Arg Leu Ala
1               5                   10                  15

Asp Tyr Leu Pro Pro Pro Ala Ala Asp Ser Ala Ala Val Ala
            20                  25                  30

Asp Leu Gly Ala Val Leu Glu Ala Gln Arg Leu Arg Thr Pro Glu Gln
        35                  40                  45

Val Arg Arg Val Arg Ala His Asp Gln Phe Glu Asp Asn Val Phe Pro
    50                  55                  60

Phe Ala Gly Asp Leu Leu Gly Ala Ser Phe Asp Lys Glu Arg Leu Pro
65                  70                  75                  80

Leu Thr Arg Ser Phe Phe Asn Arg Ala Gln Glu Asn Leu Val Glu Val
                85                  90                  95

Leu Met Pro Ala Lys Lys His Phe Ala Arg Pro Arg Pro Tyr Glu Val
            100                 105                 110

Thr Pro Lys Val Lys Pro Val Leu Pro Pro Glu Gly Glu Ser Tyr
        115                 120                 125

Pro Ser Gly His Thr Met Asp Ser Tyr Phe Lys Ala Ser Leu Leu Ser
    130                 135                 140

Met Leu Val Pro Glu His His Asp Ala Phe Phe Ala Arg Ala Glu Glu
145                 150                 155                 160
```

His Ala Gln Ser Arg Val Leu Ala Gly Val His Phe Pro Ser Asp Leu
                165                 170                 175

Glu Gly Gly Gln Thr Ala Ala Ala Leu Val Ala Ser Leu Leu Ala
            180                 185                 190

Asp Pro Ala Val Ala Ala Asp Phe Ala Ala Val Arg Glu Glu Leu Arg
            195                 200                 205

Gly Ala Leu Gly Leu Pro Lys Leu Gln
        210                 215

<210> SEQ ID NO 18
<211> LENGTH: 217
<212> TYPE: PRT
<213> ORGANISM: Artificial Sequence
<220> FEATURE:
<223> OTHER INFORMATION: Protein translated from synthetic DNA

<400> SEQUENCE: 18

Glu Thr Ala Ala Ala Pro Tyr Pro Leu Ala His Pro Pro Arg Leu Ala
1               5                   10                  15

Asp Tyr Leu Pro Pro Pro Pro Ala Ala Asp Ser Ala Ala Ala Val Ala
            20                  25                  30

Asp Leu Gly Ala Val Leu Glu Ala Gln Arg Leu Arg Thr Pro Glu Gln
        35                  40                  45

Val Arg Arg Val Arg Ala His Asp Gln Trp Glu Asp Asn Val Phe Pro
    50                  55                  60

Phe Ala Gly Asp Leu Leu Gly Ala Ser Phe Asp Lys Glu Arg Leu Pro
65                  70                  75                  80

Leu Thr Arg Ser Phe Phe Asn Arg Ala Gln Glu Asn Leu Phe Glu Val
                85                  90                  95

Leu Met Pro Ala Lys Lys His Phe Ala Arg Pro Arg Pro Tyr Glu Val
            100                 105                 110

Thr Pro Lys Val Lys Pro Val Leu Pro Pro Glu Gly Glu Ser Tyr
        115                 120                 125

Pro Ser Gly His Thr Met Asp Ser Tyr Phe Lys Ala Ser Leu Leu Ser
    130                 135                 140

Met Leu Val Pro Glu His His Asp Ala Phe Phe Ala Arg Ala Glu Glu
145                 150                 155                 160

His Ala Gln Ser Arg Val Leu Ala Gly Val His Phe Pro Ser Asp Leu
                165                 170                 175

Glu Gly Gly Gln Thr Ala Ala Ala Leu Val Ala Ser Leu Leu Ala
            180                 185                 190

Asp Pro Ala Val Ala Ala Asp Phe Ala Ala Val Arg Glu Glu Leu Arg
            195                 200                 205

Gly Ala Leu Gly Leu Pro Lys Leu Gln
        210                 215

<210> SEQ ID NO 19
<211> LENGTH: 217
<212> TYPE: PRT
<213> ORGANISM: Artificial Sequence
<220> FEATURE:
<223> OTHER INFORMATION: Protein translated from synthetic DNA

<400> SEQUENCE: 19

Glu Thr Ala Ala Ala Pro Tyr Pro Leu Ala His Pro Pro Arg Leu Ala
1               5                   10                  15

Asp Tyr Leu Pro Pro Pro Pro Ala Ala Asp Ser Ala Ala Ala Val Ala

```
                    20                  25                  30
Asp Leu Gly Ala Val Leu Glu Ala Gln Arg Leu Arg Thr Pro Glu Gln
             35                  40                  45

Val Arg Val Arg Ala His Asp Gln Trp Glu Asp Asn Val Phe Pro
     50                  55                  60

Phe Ala Gly Asp Leu Leu Gly Ala Ser Phe Asp Lys Glu Arg Leu Pro
 65                  70                  75                  80

Leu Thr Arg Ser Phe Phe Asn Arg Ala Gln Glu Asn Leu Val Glu Val
                 85                  90                  95

Leu Met Pro Ala Lys Lys His Phe Ala Arg Pro Arg Pro Tyr Glu Val
                100                 105                 110

Thr Pro Lys Val Lys Pro Val Leu Pro Pro Glu Gly Glu Ser Tyr
            115                 120                 125

Pro Ser Gly His Thr Met Arg Ser Tyr Phe Lys Ala Ser Leu Leu Ser
            130                 135                 140

Met Leu Val Pro Glu His His Asp Ala Phe Phe Ala Arg Ala Glu Glu
145                 150                 155                 160

His Ala Gln Ser Arg Val Leu Ala Gly Val His Phe Pro Ser Asp Leu
                165                 170                 175

Glu Gly Gly Gln Thr Ala Ala Ala Leu Val Ala Ser Leu Leu Ala
                180                 185                 190

Asp Pro Ala Val Ala Ala Asp Phe Ala Ala Val Arg Glu Glu Leu Arg
        195                 200                 205

Gly Ala Leu Gly Leu Pro Lys Leu Gln
        210                 215

<210> SEQ ID NO 20
<211> LENGTH: 217
<212> TYPE: PRT
<213> ORGANISM: Artificial Sequence
<220> FEATURE:
<223> OTHER INFORMATION: Protein translated from synthetic DNA

<400> SEQUENCE: 20

Glu Thr Ala Ala Ala Pro Tyr Pro Leu Ala His Pro Pro Arg Leu Ala
 1               5                  10                  15

Asp Tyr Leu Pro Pro Pro Ala Ala Asp Ser Ala Ala Ala Val Ala
             20                  25                  30

Asp Leu Gly Ala Val Leu Glu Ala Gln Arg Leu Arg Thr Pro Glu Gln
             35                  40                  45

Val Arg Val Arg Ala His Asp Gln Trp Glu Asp Asn Val Phe Pro
     50                  55                  60

Phe Ala Gly Asp Leu Leu Gly Ala Ser Phe Asp Lys Glu Arg Leu Pro
 65                  70                  75                  80

Leu Thr Arg Ser Phe Phe Asn Arg Ala Gln Glu Asn Leu Phe Glu Val
                 85                  90                  95

Leu Met Pro Ala Lys Lys His Phe Ala Arg Pro Arg Pro Tyr Glu Val
                100                 105                 110

Thr Pro Lys Val Lys Pro Val Leu Pro Pro Glu Gly Glu Ser Tyr
            115                 120                 125

Pro Ser Gly His Thr Met Arg Ser Tyr Phe Lys Ala Ser Leu Leu Ser
            130                 135                 140

Met Leu Val Pro Glu His His Asp Ala Phe Phe Ala Arg Ala Glu Glu
145                 150                 155                 160

His Ala Gln Ser Arg Val Leu Ala Gly Val His Phe Pro Ser Asp Leu
```

165                 170                 175

Glu Gly Gly Gln Thr Ala Ala Ala Leu Val Ala Ser Leu Leu Ala
            180                 185                 190

Asp Pro Ala Val Ala Ala Asp Phe Ala Val Arg Glu Glu Leu Arg
            195                 200                 205

Gly Ala Leu Gly Leu Pro Lys Leu Gln
            210                 215

<210> SEQ ID NO 21
<211> LENGTH: 217
<212> TYPE: PRT
<213> ORGANISM: Artificial Sequence
<220> FEATURE:
<223> OTHER INFORMATION: Protein translated from synthetic DNA

<400> SEQUENCE: 21

Glu Thr Ala Ala Ala Pro Tyr Pro Leu Ala His Pro Pro Arg Leu Ala
1               5                   10                  15

Asp Tyr Leu Pro Pro Pro Ala Ala Asp Ser Ala Ala Ala Val Ala
            20                  25                  30

Asp Leu Gly Ala Val Leu Glu Ala Gln Arg Leu Arg Thr Pro Glu Gln
        35                  40                  45

Val Arg Val Arg Ala His Asp Gln Pro Glu Asp Asn Val Phe Pro
50                  55                  60

Phe Ala Gly Asp Leu Leu Gly Ala Ser Phe Asp Lys Glu Arg Leu Pro
65                  70                  75                  80

Leu Thr Arg Ser Phe Phe Asn Arg Ala Gln Glu Asn Leu Val Glu Val
                85                  90                  95

Leu Met Pro Ala Lys Lys His Phe Ala Arg Pro Arg Pro Tyr Glu Val
            100                 105                 110

Thr Pro Lys Val Lys Pro Val Leu Pro Pro Glu Gly Glu Ser Tyr
            115                 120                 125

Pro Ser Gly His Thr Met Arg Ser Tyr Phe Lys Ala Ser Leu Leu Ser
    130                 135                 140

Met Leu Val Pro Glu His His Asp Ala Phe Phe Ala Arg Ala Glu Glu
145                 150                 155                 160

His Ala Gln Ser Arg Val Leu Ala Gly Val His Phe Pro Ser Asp Leu
                165                 170                 175

Glu Gly Gly Gln Thr Ala Ala Ala Leu Val Ala Ser Leu Leu Ala
            180                 185                 190

Asp Pro Ala Val Ala Ala Asp Phe Ala Val Arg Glu Glu Leu Arg
            195                 200                 205

Gly Ala Leu Gly Leu Pro Lys Leu Gln
            210                 215

<210> SEQ ID NO 22
<211> LENGTH: 217
<212> TYPE: PRT
<213> ORGANISM: Artificial Sequence
<220> FEATURE:
<223> OTHER INFORMATION: Protein translated from synthetic DNA

<400> SEQUENCE: 22

Glu Thr Ala Ala Ala Pro Tyr Pro Leu Ala His Pro Pro Arg Leu Ala
1               5                   10                  15

Asp Tyr Leu Pro Pro Pro Ala Ala Asp Ser Ala Ala Ala Val Ala
            20                  25                  30

```
Asp Leu Gly Ala Val Leu Glu Ala Gln Arg Leu Arg Thr Pro Glu Gln
        35                  40                  45

Val Arg Arg Val Arg Ala His Asp His Pro Glu Asp Asn Val Phe Pro
    50                  55                  60

Phe Ala Gly Asp Leu Leu Gly Ala Ser Phe Asp Lys Glu Arg Leu Pro
 65                  70                  75                  80

Leu Thr Arg Ser Phe Phe Asn Arg Ala Gln Glu Asn Leu Val Glu Val
                85                  90                  95

Leu Met Pro Ala Lys Lys His Phe Ala Arg Pro Arg Pro Tyr Glu Val
            100                 105                 110

Thr Pro Lys Val Lys Pro Val Leu Pro Pro Pro Glu Gly Glu Ser Tyr
        115                 120                 125

Pro Ser Gly His Thr Met Arg Ser Tyr Phe Lys Ala Ser Leu Leu Ser
        130                 135                 140

Met Leu Val Pro Glu His His Asp Ala Phe Phe Ala Arg Ala Glu Glu
145                 150                 155                 160

His Ala Gln Ser Arg Val Leu Ala Gly Val His Phe Pro Ser Asp Leu
                165                 170                 175

Glu Gly Gly Gln Thr Ala Ala Ala Leu Val Ala Ser Leu Leu Ala
                180                 185                 190

Asp Pro Ala Val Ala Ala Asp Phe Ala Ala Val Arg Glu Glu Leu Arg
        195                 200                 205

Gly Ala Leu Gly Leu Pro Lys Leu Gln
        210                 215
```